United States Patent
Kawakatsu et al.

(10) Patent No.: US 9,295,763 B2
(45) Date of Patent: Mar. 29, 2016

(54) MEDICAL TUBE

(75) Inventors: Yuta Kawakatsu, Yokkaichi (JP); Shigeo Tsuchiya, Yokkaichi (JP); Masaharu Yamada, Yokkaichi (JP); Tomoya Ohashi, Yokkaichi (JP); Wataru Takahama, Ohtsu (JP)

(73) Assignee: TOYOBO CO., LTD., Osaka-shi (JP)

( * ) Notice: Subject to any disclaimer, the term of this patent is extended or adjusted under 35 U.S.C. 154(b) by 0 days.

(21) Appl. No.: 14/126,123

(22) PCT Filed: Aug. 8, 2012

(86) PCT No.: PCT/JP2012/070162
§ 371 (c)(1),
(2), (4) Date: Dec. 13, 2013

(87) PCT Pub. No.: WO2013/027579
PCT Pub. Date: Feb. 28, 2013

(65) Prior Publication Data
US 2014/0114260 A1   Apr. 24, 2014

(30) Foreign Application Priority Data

Aug. 19, 2011 (JP) ................................ 2011-179394

(51) Int. Cl.
| | | |
|---|---|---|
| *A61M 5/32* | (2006.01) | |
| *A61L 33/00* | (2006.01) | |
| *A61L 33/06* | (2006.01) | |
| *A61L 33/08* | (2006.01) | |
| *A61L 29/16* | (2006.01) | |
| *A61M 39/08* | (2006.01) | |
| *A61M 1/36* | (2006.01) | |
| *A61M 25/00* | (2006.01) | |

(52) U.S. Cl.
CPC ............. *A61L 33/0094* (2013.01); *A61L 29/16* (2013.01); *A61L 33/0011* (2013.01); *A61L 33/068* (2013.01); *A61L 33/08* (2013.01); *A61M 1/3673* (2014.02); *A61M 39/08* (2013.01); *A61L 2300/42* (2013.01); *A61M 25/0009* (2013.01); *A61M 25/0045* (2013.01); *A61M 2025/0047* (2013.01); *A61M 2205/0238* (2013.01)

(58) Field of Classification Search
CPC .................... A61M 25/0009; A61M 25/0045; A61M 2025/0047; A61M 2205/0238; A61M 39/08; A61M 1/3673; A61L 33/068; A61L 29/16; A61L 33/0011; A61L 2300/42; A61L 33/08; A61L 33/0094; C08L 33/08
See application file for complete search history.

(56) References Cited

U.S. PATENT DOCUMENTS

2010/0135852 A1 * 6/2010 Kawakatsu et al. ............. 422/48

FOREIGN PATENT DOCUMENTS

| | | |
|---|---|---|
| WO | 02/098344 A1 | 12/2002 |
| WO | 2011/083815 A1 | 7/2011 |

OTHER PUBLICATIONS

International Search Report for PCT/JP2012/027579, Mailing Date of Oct. 2, 2012.
Extended European Search Report dated Aug. 19, 2015, issued in counterpart application No. 12825489.3 (7 pages).
"Why Are They Important? The Effects of Humidity and (Dew-point) Temperature on Ambient Cure Epoxy Coatings.", Dec. 1, 2007, www.dow.com/scripts/litorder.asp?filepath=/296-01667, p. 1; cited in Extended European Search Report dated Aug. 19, 2015.

* cited by examiner

*Primary Examiner* — Suzanne Ziska
(74) *Attorney, Agent, or Firm* — Westerman, Hattori, Daniels & Adrian, LLP

(57) ABSTRACT

The present invention provides a medical tube mainly comprising a thermoplastic resin wherein the surface contacting the blood has been subjected to a heparinizing treatment and wherein quality defect due to whitening and oil defect is reduced.

According to the present invention, there is provided a medical tube wherein an antithrombotic material is coated on the inner surface of a tube prepared by a melt extrusion molding of a composition comprising a thermoplastic resin and a plasticizer, characterized in that the difference (ΔL) between the brightness of the medical tube before coating and the brightness of the medical tube after coating measured in accordance with JIS Z 8722 is 1 or less.

4 Claims, 2 Drawing Sheets

MEDICAL TUBE

TECHNICAL FIELD OF THE INVENTION

The present invention relates to a medical tube which is used as a main tube or the like constituting the blood circuit for artificial dialysis and cardiopulmonary bypass. More particularly, it relates to a medical tube wherein the surface contacting the blood has been subjected to a heparinizing treatment and wherein appearance defect such as turbidity and oil defect by the above treatment is reduced.

BACKGROUND ART

A medical tube has been used in very many medical devices such as an infusion set for administration of infusion fluid from infusion bag, a transfusion set used in the same manner as above for the transfusion, a blood bag used for collection of blood from humans such as blood donation and circuits used in the application of blood dialysis, cardiopulmonary bypass, etc.

Up to now, polyurethane resin, silicone resin and vinyl chloride resin have been commonly used as a material for molding a medical tube. A medical tube comprising polyurethane resin has some hardness and, when it is pushed or revolved, the resulting force is apt to be transmitted to the front end whereby it exhibits good operating property and also softening property by body temperature. In the case of a medical tube comprising silicone resin, although it is flexible, it is too soft whereby its operating property is inferior. A medical tube comprising vinyl chloride resin has such characteristics that its molding property is good, its material cost and production cost are less expensive, its soft property as a tube is adequate and its processing property in assembling a medical device, etc. is good.

A technique has been also known wherein adaptability to blood is improved by immobilization of heparin on the surface contacting the blood (Refer, for example, to Patent Document 1). According to said document, a surface treatment is as follows: an ionic compound of hydrophobic organic cation mixture with hydrophilic heparin is firstly produced, dissolved in an organic solvent such as tetrahydrofuran and applied onto the surface of a medical device and, after that, the organic solvent is removed by means of drying with aeration. Although it is possible to just apply onto the surface of a medical device by such a method, there have been problems of appearance defect therein such as occurrence of turbidity (aggregation of the ionic compound) and oil defect (elution of a plasticizer) on the surface of a tube.

PRIOR ART DOCUMENTS

Patent Documents

Patent Document 1: WO 2002/098344

DISCLOSURE OF THE INVENTION

Problem that the Invention is to Solve

An object of the present invention is to provide a medical tube mainly comprising a thermoplastic resin wherein the surface contacting the blood has been subjected to a heparinizing treatment and wherein quality defect due to whitening and oil defect is reduced.

Means for Solving the Problem

The present inventors have conducted intensive investigations for achieving the above object and, as a result, they found that the above object can be achieved by a medical tube having the following constitution:

(1) A medical tube wherein an antithrombotic material is coated on the inner surface of a tube prepared by a melt extrusion molding of a composition comprising a thermoplastic resin and a plasticizer, characterized in that the difference ($\Delta L$) between the brightness of the medical tube before coating and the brightness of the medical tube after coating measured in accordance with JIS Z 8722 is 1 or less.

(2) The medical tube according to (1), wherein no oil defect is found on the tube surface.

(3) The medical tube according to (1) or (2), wherein inner diameter and thickness of the tube are 0.1 to 30 mm and 0.2 to 5 mm, respectively.

(4) The medical tube according to any of (1), (2) and (3), wherein the antithrombotic material is a heparin compound or a copolymer of hydrophobic (meth)acrylate with hydrophilic (meth)acrylate.

Advantages of the Invention

In the medical tube according to the present invention, aggregation of a material such as a heparin compound is suppressed when said material is coated on the tube surface whereby appearance defect due to turbidity can be reduced. In addition, since due consideration is paid on the drying condition for coating the material, occurrence of oil defect can be reduced.

BEST MODE FOR CARRYING OUT THE INVENTION

Figure 1:
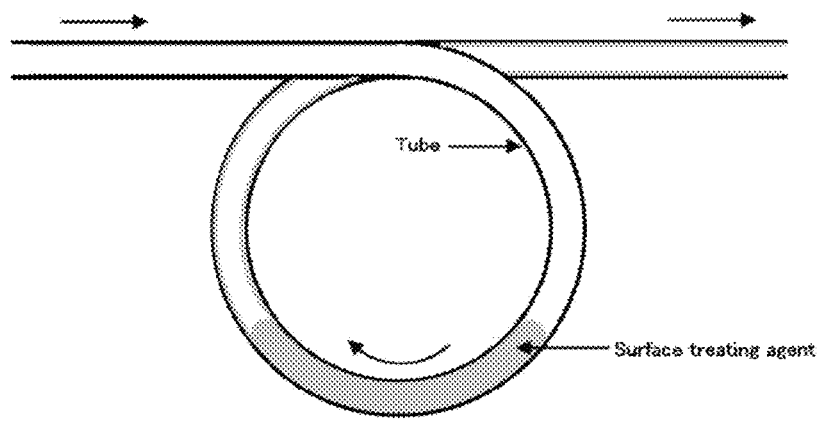
FIG. 1 is a schematic chart which shows the step for coating an antithrombotic material on the tube surface.

As roughly shown in FIG. 1, the medical tube according to the present invention is manufactured in such a manner that a solution (a surface treating agent) containing an antithrombotic material dissolved therein is introduced into a tube which is installed in a convex shape or a loop shape directed downwardly and then the tube is advanced in a direction of an arrow so that the antithrombotic material is coated onto the inner surface of the tube. The characteristic features of the medical tube according to the present invention are not only that there is no whitening phenomenon by aggregation of an antithrombotic material after coating the antithrombotic material onto the inner area of the tube followed by drying but also that there is no oil defect due to elution of a plasticizer. Therefore, as compared with the conventional tubes, the medical tube according to the present invention has advantages of high quality and high safety such as that contamination of air bubbles in the blood passing through the inner area of the tube can be easily confirmed and that adhesion of thrombocyte and production of thrombus can be suppressed.

Examples of the antithrombotic material are heparin and its derivatives, a material derived from living body such as an ionic complex of heparin or heparin derivative with an organic cation mixture, a homopolymer of hydrophobic (meth)acrylate or hydrophilic (meth)acrylate, a copolymer of hydrophobic (meth)acrylate with hydrophilic (meth)acrylate, and a synthetic polymer material such as a polymer having a phospholipid polar group. Any of them can be used in the present invention.

With regard to a solvent for dissolving the antithrombotic material, although there is no particular limitation so far as it does not deteriorate the antithrombotic property of the antithrombotic material and does not damage the surface of the medical tube, there may be used, for example, methanol, ethanol, isopropyl alcohol, n-propyl alcohol, n-hexane, cyclohexane, tetrahydrofuran, 1,4-dioxane, cyclohexanone, N,N-dimethylformamide, N,N-dimethylacetamide and N-methylpyrrolidone in the present invention.

Concentration of the antithrombotic material in the surface treating agent is preferred to be 0.05 to 0.5% by weight. When the concentration is too low, sufficient antithrombotic property may not be imparted to the medical tube or it is necessary to repeat the coating treatment frequency and that is not economical. When the concentration is too high, the antithrombotic material is apt to aggregate whereby the whitening may not be suppressed. The concentration is more preferred to be 0.1 to 0.4% by weight and further preferred to be 0.2 to 0.3% by weight. In addition, it is not excluded that, besides the antithrombotic material, an antibacterial material or the like is further added to the surface treating agent.

After the appropriate amount of the above-prepared surface treating agent is flown into the inner area of the tube set up in a loop shape as shown in FIG. 1, the tube is advanced in the lengthwise direction so that the surface treating agent moves from the inlet of the tube to the outlet of the tube while contacting the inner surface of the tube at all times.

Although the radius of the loop at this time may depend upon the radius of the tube, it is preferred to be about 10 cm to 50 cm. When the radius is too large, it is then necessary to increase the liquid amount of the surface treating agent whereupon the plasticizer is apt to be eluted and oil defect may happen. Thus, when the moving speed of the tube is made high so as to shorten the contacting time of the surface treating agent to the inner surface of the tube, liquid drops of the surface treating agent are apt to remain on the inner wall surface of the tube whereby the plasticizer is eluted in the remained area. On the other hand, when the moving speed is made slow so that the liquid drops do not remain, contacting time of the surface treating agent per unit surface area of the tube becomes long whereby the plasticizer is apt to be eluted. When the radius of the loop is too small, operating ability of the surface treatment may be deteriorated and the liquid amount of the surface treating agent to be introduced into the tube needs to be reduced unnecessarily whereby the length of the tube which can be treated at a time becomes short.

The inner diameter of the medical tube is preferred to be 0.1 to 30 mm. When the inner diameter is too small, the affection by surface tension is apt to happen or the air bubbles are easily caught whereby the surface treating operation may sometimes be hardly conducted. On the other hand, when the inner diameter of the tube is too large, that is not advantageous in industrial view because it is now necessary to severely control the moving speed of the tube so as to make the liquid drop residue and the contacting time well balanced as mentioned above. Accordingly, the inner diameter of the tube is more preferred to be 1 to 25 mm and further preferred to be 2 to 20 mm.

Although the thickness of the tube is not particularly limited, it is preferred to be 0.2 to 5 mm. When the thickness is too thin, the strength may sometimes become low. When the thickness is too thick, the softness of the tube may be insufficient or visibility of the inner area may lower. Accordingly, the thickness of the tube is more preferred to be 0.6 to 4 mm and further preferred to be 1 to 3 mm.

With regard to the length of the tube to be subjected to a surface treatment in the present invention, it is preferred to be 3 m or longer in view of the productive efficiency. When the tube length is too long, it is now necessary to introduce a surface treating agent corresponding to such a length. In that case, time for contacting the surface treating agent per unit area becomes long whereby a possibility of causing the oil defect increases. Therefore, the length of the tube for conducting the surface treatment at a time is preferred to be 20 m or less. The length of the tube is more preferred to be 5 to 18 m and further preferred to be 7 to 15 m.

Arithmetic average roughness (Ra) according to JIS B 0601 (2001) of the inner and outer surfaces of the tube is preferred to be 0.001 to 0.1 µm. When the roughness of the surfaces is too much, whitening is apt to happen when an antithrombotic material is coated on the inner surface of the tube and, at the same time, there happens a problem that the measurement of brightness difference ΔL which will be mentioned later becomes difficult. Moreover, the surface treating agent is apt to remain whereby the oil defect may happen. Therefore, Ra is more preferred to be 0.005 µm to 0.09 µm and further preferred to be 0.01 µm to 0.08 µm.

The arithmetic average roughness (Ra) is the magnitude of the distribution in the height direction of the surface and the surface roughness can be expressed in terms of the numeral value. Thus, when Ra is large, the surface is rough while, when Ra is small, the surface is smooth. Although the smoothness of the surface can be expressed in terms of Rq (square average root roughness) or Rz (ten-point average roughness), evaluation by means of Ra is preferred. This is because the measured value thereby is apt to be uniform in the same sample even when the measured area is changed.

The medical tube according to the present invention is preferred to be molded using a molding solution containing a thermoplastic polymer and a plasticizer together, if necessary, with a stabilizer. Examples of the thermoplastic polymer include poly(vinyl chloride), polyamide, polycarbonate, polyethylene, polysulfone, polyether sulfone and a copolymer of ethylene with vinyl acetate. Among them, poly(vinyl chloride) is preferred in view of cost and of the fact that physical properties of the medical tube can be freely modified by adjusting the adding amount of a plasticizer.

With regard to a plasticizer, there have been used butyl benzyl phthalate, di-ethylhexyl phthalate (DOP), di-isodecyl phthalate, di-isononyl phthalate, di-hexyl phthalate, di-octyl phthalate, etc. from old times and, among them, di-ethylhexyl phthalate (DOP) is most frequently used. In recent years, there are also the cases wherein less soluble tri-diethylhexyl trimellitate (TOTM) and Hexamoll DINCH (registered trade mark) are used worrying about the risk of elution of the plasticizer.

In the medical tube according to the present invention, amount of the plasticizer contained in 100 parts by weight of the thermoplastic resin is preferred to be 50 to 120 parts by weight. Here, the term reading part (s) by weight means the weight of plasticizer contained therein when the amount of the thermoplastic resin is 100 parts by weight. When the amount of the plasticizer is too small, the softness necessary for the medical tube may be deteriorated. When the amount of the plasticizer is too much, poor dissolution of the plasticizer is resulted and transparency of the tube may be deteriorated. In addition, when the amount of the plasticizer is too much, the coating may be detached or the coating spots may be occurred upon application of the coating on the tube surfaces.

Therefore, amount of the plasticizer is more preferred to be 60 to 110 parts by weight and further preferred to be 65 to 100 parts by weight.

Examples of the stabilizer include a metal compound comprising organic acid salt (metal soap), inorganic acid salt, organic tin compound and other organic metal compound and a non-metal compound comprising organic phosphorus compound, epoxy compound, antioxidant and ultraviolet absorber. In view of safety in the medical use, preferred ones are heavy metal-free organic acid salt, organic phosphorus compound and epoxy compound.

Although the amount of a surface treating agent to be introduced into the inner area of the tube depends upon the inner diameter of the tube and the diameter of the loop, it is preferred to be 0.1 to 10 mL/m. When the amount is below the above range, the whole inner surface cannot be uniformly treated. Thus, there is a risk of causing the difference in the concentrations of the antithrombotic agent between the inlet side and the outlet side of the tube and that is not preferred. When the amount exceeds the above range, the production cost rises or the oil defect is resulted due to elution of the plasticizer and that is not preferred. The amount of the surface treating agent is more preferred to be 0.2 to 9 mL/m and further preferred to be 0.3 to 8 mL/m.

The velocity of the surface treating agent passing through the inner area of the tube according to the present invention is preferred to be 0.5 to 6 m/min. When the passing velocity is below the above range, not only the productive efficiency lowers but also the oil defect is apt to happen and that is not preferred. When the passing velocity exceeds the above range, liquid drops of the surface treating agent remain on the inner wall side of the tube causing the oil defect and that is not preferred. The passing velocity is more preferred to be 1 to 5 m/min and further preferred to be 1.5 to 4 m/min.

After the residual surface treating agent solution is removed from the tube wherein the antithrombotic material has been coated on the inner wall side under the above-mentioned condition, the residual solvent is removed by means of a drying treatment.

When the medical tube is dried under the specific condition which will be mentioned later, occurrence of whitening phenomenon due to aggregation of the antithrombotic material can be suppressed. Occurrence of the oil defect due to elution of the plasticizer can be suppressed as well.

Thus, as to the drying air, it is preferred in the present invention to use the air having a dew point of not higher than −15° C. When the drying air having a dew point of higher than −15° C. is used, it is unavoidable to form a coat near the end of the tube which is apt to contact the outer air and there is such a risk thereby that thrombus is generated at the detached area upon flowing the blood or that the detached pieces block the peripheral blood vessel. In addition, the lower the dew point of the drying air in the present invention, the less the water amount on the treating surface whereby growth of the bacteria existing in the air can be suppressed. The tube of the present invention is subjected to a sterilizing treatment before circulation in the market whereby the living microbes are dead but the dead ones remain as endotoxin on the inner surface of the tube. When endotoxin comes into blood vessel, it results in toxic action such as fever, vascular endothelial cell disorder or accentuated capillary transmission whereby it is preferred to reduce the amount of endotoxin on the surface contacting the blood to be subjected to a surface treatment. Accordingly, the dew point of the drying air is more preferably not higher than −30° C., and further preferably not higher than −45° C.

As to affection of the dew point of the drying air on the whitening, a surficial cooling of the tube due to the flow of the drying air may be exemplified. This cooling is occurred when an organic solvent in the surface treating agent is evaporated and proceeds as long as the evaporation continues. When the temperature on the inner surface of the tube reaches below the dew point of the air existing therein as a result of cooling, water droplets stick on the inner surface of the tube. It is likely that solubility of the lipophilic antithrombotic material lowers due to the stuck water droplets whereby aggregation and precipitation are resulted causing the whitening.

In the whitened area, the antithrombotic material is partially concentrated and the film is thick. Accordingly, there is a risk of detachment of the film even under the usually applied blood flow. If the film is detached, the tube directly contacts the blood and thrombus is generated at the area where detachment of the film happens. There is a risk that such thrombus generated in the inner area of the medical tube is carried into the blood flow and clogs the microvessel such as capillary vessel causing severe damage. Because of the above, it is necessary to suppress the whitening on the inner surface of the tube as much as possible.

The inventors investigated a method for the evaluation of whitening of the tube, and found that brightness (L value) measured in accordance with JIS Z 8722 is useful. Reflected light is measured by applying light to the outer surface of the tube having the length of 5 cm using a high-speed spectrophotometer (CMS-35SP) manufactured by Murakami Color Research Laboratory. The value ΔL which is the difference between the L value obtained for the tube after the surface treatment and the L value obtained for the tube before the surface treatment is determined by the following formula. In this formula, L1 is the L value of the untreated tube and L2 is the L value of the whitened area.

$$\Delta L = L1 - L2$$

Figure 2:
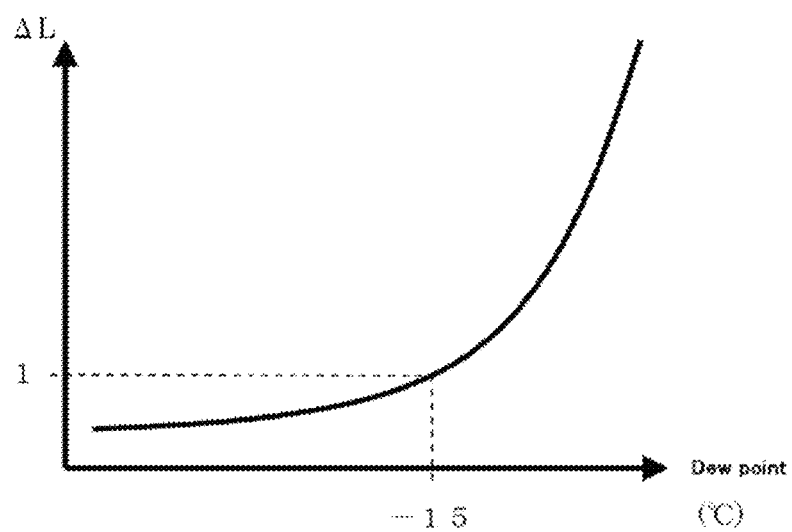
FIG. 2 is a graph which shows the relation between the dew point of drying air and the whitening (brightness difference $\Delta L$).

The present inventors have checked the relation between the dew point of the drying air and the whitening (brightness difference ΔL). The result is schematically shown in FIG. 2. An abscissa of FIG. 2 is the dew point of the drying air and an ordinate is ΔL which is the index for the whitening. It is noted from FIG. 2 that the lower the dew point of the air, the less the ΔL. It is also noted that ΔL reaches about 1 when the air having a dew point of about −15° C. is used. Thus, for making ΔL 1 or less, it is found that, although there is the influence of the outer temperature, aggregation of the antithrombotic material caused by water in the drying air can be suppressed if the air having a dew point of not higher than −15° C. or so is used in the case of the treatment at room temperature and that the whitening can be suppressed as well. It has been also confirmed that, when ΔL is less than 1, detachment of the film from the whitened area can be well suppressed.

Linear velocity of the drying air is preferred to be 5 to 350 m/min, more preferred to be 10 to 300 m/min, and further preferred to be 15 to 250 m/min. It is preferred that the flow rate of the air is within such a range because occurrence of the oil defect due to elution of a plasticizer can be suppressed and whitening of the surface by an excessive flow rate can be reduced thereby.

When the linear velocity (flow rate) of the drying air is too low, drying does not proceed whereby contacting time of the inner surface of the tube to the solvent increases and elution of the plasticizer contained in the medical tube is promoted. When the elution becomes significant, removal of the plasticizer which is once eluted is difficult and, finally, appearance defect is resulted as the oil defect. When flow rate of the drying air is made low and much plasticizer is extracted, it is very difficult to solve the problem of the oil defect even if the tube is placed in a drying machine or the like and the drying is promoted by heating since the plasticizer has a high boiling point. Moreover, since the tube becomes soft when the temperature becomes high, there is also a possibility that inner and outer diameters of the tube become large due to the influence of the air pressure passing through the inside. On the contrary, when the linear velocity (flow rate) of the drying air becomes too high, it is necessary to use the air having lower dew point and that is disadvantageous in view of economy.

As to a method confirming the oil defect, there is exemplified a method wherein the tube in which the inner surface is treated is exposed to light source such as a fluorescent lamp and confirmation is conducted by naked eye from the lengthwise direction. Outline of the oil defect can be confirmed by naked eye from the difference between the refractive indexes of the tube and the plasticizer constituting the oil defect.

In the tube having no oil defect in the inner surface, eluting amount of the plasticizer into the blood can be reduced upon contacting the blood in actual use. The plasticizer to be added for softening the material is abundantly contained in the medical tube and its toxicity is being worried about in some types of the plasticizer. If the oil defect exists, the elution into the blood is promoted further. Therefore, it is necessary that no oil defect exists.

As to a method for evaluating the coloration of the medical tube according to the present invention, a method of JIS K 0071-1 has been known. Thus, degree of coloration can be expressed in terms of Hazen units. When coloration of the medical tube is 0 to 100 Hazen units, the inner area of the medical tube can be well confirmed visually whereby that is preferable. When Hazen units are outside this range, brightness is low even in the untreated tube and difference from the treated one is hardly noted whereby that is not preferred. Thus, 80 or less is more preferred and 60 or less is further preferred. In addition, 20 or greater is more preferred and 30 or greater is further preferred.

EXAMPLES

The present invention will now be illustrated in more detail as hereunder by Examples although the present invention is not limited to these Examples. Incidentally, the characteristic values in the Examples were measured by the following methods.

(Measurement of Inner and Outer Diameters of Tube)

Inner and outer diameters of a tube were measured using a projector (V-12B manufactured by Nikon). Thus, a tube was cut into 3-mm thickness using a hose cutter (HC03) to prepare a sample. Magnification was set 10-fold. A stage was moved so that lower right area of the outer surface of a sample contacted X and Y axes by checking the projection to reset the X and Y coordinates and then the stage was moved to the place where the upper left area of the outer surface of the sample contacted the X and Y axes whereupon the mean value A of X and Y coordinates was taken. Then the stage was further moved so that X and Y axes contacted the upper right area of the outer surface of the sample, the values of the X and Y coordinates were reset, then X and Y coordinates were moved so as to contact the lower left area of the outer surface of the sample, and the mean value B of the values of X and Y coordinates was taken. The mean value C of A and B was adopted as the value of an outer diameter. Similar measurement was also conducted for the inner surface as well and the value of inner diameter was calculated.

(Measurement of Surface Roughness)

A tube was cut out in a length of about 2 cm to open, its inner or outer surface was made upside and placed on a sample stand and the surrounding was pushed so that the surface was made as flat as possible followed by fixing. A recess/salient picture of the inner or outer surface was prepared under the condition wherein the objective lens was in 50 magnifications and the height pitch was 0.05 µm, using a co-focal laser microscope VK-8500 manufactured by Keyence. The resulting recess/salient picture was subjected to a correction for inclination (surface correction (automatic)) and then the surface roughness (Ra) within an area of 100 µm×100 µm was determined.

(Measurement of Coloration)

A standard solution (30 mL) having Hazen units of 0 to 500 being adjusted according to JIS K 0071-1 (with intervals of 10 units) was placed in a 30-mL glass vial (catalog name: As One; product name: laboratory screw tube bottle; product number: 9-582-08). As to a sample, that which was cut into about 5 cm in a lengthwise direction using a hose cutter (HC03) was used. For each of the sample and the standard solution, the color was compared by naked eye in a uniaxial direction and the color unit of the nearest standard solution was adopted as the color unit of the sample. For example, when the color unit of the sample was between the units 50 and 60 of the standard solutions, the color unit of the sample was decided to be 60.

(Measurement of Oil Defect)

The treated tube was confirmed by naked eye from the lengthwise direction at the position of being about 1 m apart from a fluorescent lamp (white fluorescent lamp (cylindrical type) [Sunline] rapid start form, type 40: FLR 40S-W/M/36-B, manufactured by Hitachi). The case wherein oily outline could not be confirmed by naked eye, it was expressed as "not noted" while the case wherein oily outline could be confirmed, it was expressed as "noted".

(Measurement of ΔL)

Figure 3:
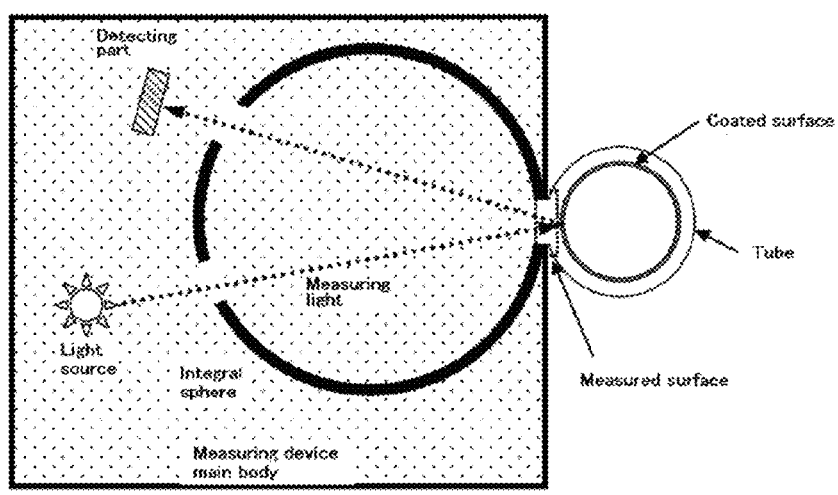
FIG. 3 is a schematic drawing which shows an example of measurement of brightness (L value) of the tube of the present invention.

As shown in FIG. 3, the measurement was conducted using a high-speed spectrophotometer (CMS-35SP) manufactured by Murakami Color Research Laboratory in such a manner that a tube in the length of about 5 cm was fixed so that the outer surface thereof contacted an integral sphere. The value ΔL which is the difference between the L value obtained for the tube after the surface treatment and the L value obtained for the tube before the surface treatment is determined by the following formula. In this formula, L1 is the L value of the untreated tube and L2 is the L value of the whitened area.

$$\Delta L = L1 - L2$$

(Measurement of Endotoxin)

Distilled water for injection (manufactured by Otsuka) was filled in a tube after the surface treatment and the treated surface was aseptically extracted to give an extract. The resulting extract was measured using an Endosafe-PTS reader and PTS cartridge JP (1 to 0.01 EU/ml) manufactured by Wako Pure Chemical Industries). When endotoxin was detected, it was expressed as "found" and, when not detected, it was expressed as "not found".

(Preparation of Surface Treating Agent 1)

Dodecylbenzyldimethylammonium bromide (manufactured by Tokyo Kasei) (20 parts by weight) and 60 parts by weight of ditetradecyldimethylammonium bromide (manufactured by Tokyo Kasei) were dissolved in 150 parts by weight of methanol. After confirming that they were completely dissolved, water was added to this methanolic solution of the organic ammoniums until the ratio of [methanolic solution:water] reached [30:70 by weight]. At that time, the ammonium salts were partially separated in the solution but a homogeneous solution was resulted upon raising the temperature of the solution up to 50° C.

Heparin sodium (30 parts by weight) was dissolved in 150 parts by weight of deionized water. After that, methanol was added to this aqueous heparin solution until the ratio of [aqueous heparin solution:methanol] reached [30:70 by weight]. At that time, heparin was partially separated in the solution whereby the solution became a suspension state but a homogeneous solution was resulted upon raising the temperature of the solution up to 70° C.

The above ammonium salt solution was dropped into the resulting heparin solution with stirring. The reaction product was immediately precipitated in the solution. The precipitate was recovered and well washed to remove the unreacted heparin and ammonium salts. The residue was centrifuged to remove water and then subjected to freeze-drying to give a heparinized preparation. It was further dissolved in tetrahydrofuran (THF) for giving a predetermined concentration whereupon a surface treating agent 1 was prepared.

(Preparation of Surface Treating Agent 2)

To a reactor being able to be stirred and equipped with a refluxing tower were added 15.1 g of methoxytriethylene glycol acrylate (MTEGA) (manufactured by Shin Nakamura Kagaku Kogyo), 29.7 g of 2-ethylhexyl acrylate (EHA) (manufactured by Tokyo Kasei Kogyo), 0.0447 g of azobisisobutyronitrile (AIBN) (manufactured by Wako Pure Chemical Industries) and 178.9 g of ethyl acetate (manufactured by Tokyo Kasei Kogyo) followed by subjecting to a polymerization reaction at 80° C. for 20 hours. In the meanwhile, the inner area of the reactor was previously substituted with nitrogen and, during the polymerization reaction, bubbling with nitrogen was continued. After completion of the polymerization reaction, the solvent for polymerization was removed by evaporation for four days under the condition of 60° C. and 1 Torr to give a crude (meth)acrylate copolymer. The resulting crude (meth)acrylate copolymer (2 g) was dissolved in 2 g of tetrahydrofuran (THF) and dropped into 20 g of a poor solvent (comprising methanol and water in a ratio by weight of 80/20) under stirring using a Pasteur pipette. An operation comprising that the precipitate was recovered by means of decantation, dissolved again by addition of THF in the same weight and dropped into a poor solvent was repeated twice and, after that, drying in vacuo was carried out for four days under the vacuum condition of 0.1 Torr at 60° C. The resulting pure product was dissolved in THF so that a predetermined concentration was achieved to give a surface treating agent 2.

(Preparation of Surface Treating Agent 3)

To a reactor being able to be stirred and equipped with a refluxing tower were added 17.8 g of methoxytriethylene glycol acrylate (MTEGA) (manufactured by Shin Nakamura Kagaku Kogyo), 4.8 g of silicone methacrylate (manufactured by Shin-Etsu Chemical Co., Ltd., product name: X-24-8201, number average molecular weight: 2100), 27.5 g of 2-ethylhexyl acrylate (EHA) (manufactured by Tokyo Kasei Kogyo), 0.0447 g of azobisisobutyronitrile (AIBN) (manufactured by Wako Pure Chemical Industries) and 200.2 g of ethyl acetate (manufactured by Tokyo Kasei Kogyo) followed by subjecting to a polymerization reaction at 80° C. for 20 hours. In the meanwhile, the inner area of the reactor was previously substituted with nitrogen and, during the polymerization reaction, bubbling with nitrogen was continued. After completion of the polymerization reaction, the solvent for polymerization was removed by evaporation for four days under the condition of 60° C. and 1 Torr to give a crude (meth)acrylate copolymer. The resulting crude (meth)acrylate copolymer (2 g) was dissolved in 2 g of tetrahydrofuran (THF) and dropped into 20 g of a poor solvent (comprising methanol and water in a ratio by weight of 80/20) under stirring using a Pasteur pipette. An operation comprising that the precipitate was recovered by means of decantation, dissolved again by addition of THF in the same weight and dropped into a poor solvent was repeated twice and, after that, drying in vacuo was carried out for four days under the vacuum condition of 0.1 Torr at 60° C. The resulting pure product was dissolved in THF so that a predetermined concentration was achieved to give a surface treating agent 3.

(Method of Preparing a Tube)

A composition (in pellets) comprising poly(vinyl chloride) resin and di-2-ethylhexyl phthalate (DOP) was provided to a providing part (hopper) and transferred into a cylinder. Screw having compression ratio of 4 was rotated at 56.0 rpm and the pellets were transferred to the front area of the cylinder by melting them at the cylinder temperature of 170° C. The resulting melted resin was extruded from spiral dies of the outlet area of the cylinder. Temperature of the resin at the outlet area of the cylinder at that time was 188° C. The melted resin extruded therefrom was passed through a vacuum water tank having the temperature of 15° C. and then cooled down to nearly the room temperature using the cooling water tank of the same temperature. Degree of vacuum of the vacuum water tank at that time was made −7.0 kPa. The resulting tube was wound around a winding machine at a pulling speed of 10 m/min.

Example 1

There was prepared a tube comprising 72.0 parts by weight of di-2-ethylhexyl phthalate (DOP) to 100 parts by weight of poly(vinyl chloride) resin and having the inner diameter of 12.7 mm, the outer diameter of 17.3 mm and the total length of 7 m. The resulting tube was subjected to a surface treatment using the surface treating agent 1 in a concentration of 0.3 wt %. Said tube was made into a loop of 30 cm radius as shown in FIG. 1, then 30 mL of the surface treating agent 1 in said concentration was placed therein. The tube was moved at the speed of 3.8 m/min and the surface treating agent 1 was flown therein until it reaches the outlet side. After removing the residual surface treating agent, air having a dew point of −15° C. was flown into the tube for 3 minutes at the linear velocity of 16 m/min to dry.

Example 2

There was prepared a tube comprising 72.0 parts by weight of di-2-ethylhexyl phthalate (DOP) to 100 parts by weight of poly (vinyl chloride) resin and having the inner diameter of 6.4 mm, the outer diameter of 11.0 mm and the total length of 10 m. The resulting tube was subjected to a surface treatment using the surface treating agent 1 in a concentration of 0.3 wt %. Said tube was made into a loop of 30 cm radius as shown in FIG. 1, then 13 mL of the surface treating agent 1 in said concentration was placed therein. The tube was moved at the speed of 2.8 m/min and the surface treating agent 1 was flown therein until it reaches the outlet side. After removing the residual surface treating agent, air having a dew point of −15° C. was flown into the tube for 3 minutes at the linear velocity of 63 m/min to dry.

Example 3

There was prepared a tube comprising 72.0 parts by weight of di-2-ethylhexyl phthalate (DOP) to 100 parts by weight of poly (vinyl chloride) resin and having the inner diameter of 12.7 mm, the outer diameter of 17.3 mm and the total length of 7 m. The resulting tube was subjected to a surface treatment using the surface treating agent 1 in a concentration of 0.2 wt %. Said tube was made into a loop of 30 cm radius as shown in FIG. 1, then 30 mL of the surface treating agent 1 in said concentration was placed therein. The tube was moved at the speed of 3.8 m/min and the surface treating agent 1 was flown therein until it reaches the outlet side. After removing the residual surface treating agent, air having a dew point of −45° C. was flown into the tube for 3 minutes at the linear velocity of 16 m/min to dry.

Example 4

There was prepared a tube comprising 72.0 parts by weight of di-2-ethylhexyl phthalate (DOP) to 100 parts by weight of poly(vinyl chloride) resin and having the inner diameter of 6.4 mm, the outer diameter of 11.0 mm and the total length of 10 m. The resulting tube was subjected to a surface treatment using the surface treating agent 1 in a concentration of 0.2 wt %. Said tube was made into a loop of 30 cm radius as shown in FIG. 1, then 13 mL of the surface treating agent 1 in said concentration was placed therein. The tube was moved at the speed of 2.8 m/min and the surface treating agent 1 was flown therein until it reaches the outlet side. After removing the residual surface treating agent, air having a dew point of −45° C. was flown into the tube for 3 minutes at the linear velocity of 63 m/min to dry.

Example 5

There was prepared a tube comprising 72.0 parts by weight of di-2-ethylhexyl phthalate (DOP) to 100 parts by weight of poly(vinyl chloride) resin and having the inner diameter of 12.7 mm, the outer diameter of 17.3 mm and the total length of 7 m. The resulting tube was subjected to a surface treatment using the surface treating agent 1 in a concentration of 0.3 wt %. Said tube was made into a loop of 30 cm radius as shown in FIG. 1, then 30 mL of the surface treating agent 1 in said concentration was placed therein. The tube was moved at the speed of 3.8 m/min and the surface treating agent 1 was flown therein until it reaches the outlet side. After removing the residual surface treating agent, air having a dew point of −15° C. was flown into the tube for 3 minutes at the linear velocity of 3 m/min to dry.

Example 6

There was prepared a tube comprising 72.0 parts by weight of di-2-ethylhexyl phthalate (DOP) to 100 parts by weight of poly (vinyl chloride) resin and having the inner diameter of 12.7 mm, the outer diameter of 17.3 mm and the total length of 7 m. The resulting tube was subjected to a surface treatment using the surface treating agent 2 in a concentration of 0.2 wt %. Said tube was made into a loop of 30 cm radius as shown in FIG. 1, then 30 mL of the surface treating agent 2 in said concentration was placed therein. The tube was moved at the speed of 3.8 m/min and the surface treating agent 2 was flown therein until it reaches the outlet side. After removing the residual surface treating agent, air having a dew point of −45° C. was flown into the tube for 3 minutes at the linear velocity of 16 m/min to dry.

Example 7

There was prepared a tube comprising 72.0 parts by weight of di-2-ethylhexyl phthalate (DOP) to 100 parts by weight of poly(vinyl chloride) resin and having the inner diameter of 12.7 mm, the outer diameter of 17.3 mm and the total length of 7 m. The resulting tube was subjected to a surface treatment using the surface treating agent 3 in a concentration of 0.2 wt %. Said tube was made into a loop of 30 cm radius as shown in FIG. 1, then 30 mL of the surface treating agent 3 in said concentration was placed therein. The tube was moved at the speed of 3.8 m/min and the surface treating agent 3 was flown therein until it reaches the outlet side. After removing the residual surface treating agent, air having a dew point of −45° C. was flown into the tube for 3 minutes at the linear velocity of 16 m/min to dry.

Comparative Example 1

There was prepared a tube comprising 72.0 parts by weight of di-2-ethylhexyl phthalate (DOP) to 100 parts by weight of poly (vinyl chloride) resin and having the inner diameter of 12.7 mm, the outer diameter of 17.3 mm and the total length of 7 m. The resulting tube was subjected to a surface treatment using the surface treating agent 1 in a concentration of 0.6 wt %. Said tube was made into a loop of 30 cm radius as shown in FIG. 1, then 30 mL of the surface treating agent 1 in said concentration was placed therein. The tube was moved at the speed of 3.8 m/min and the surface treating agent 1 was flown therein until it reaches the outlet side. After removing the residual surface treating agent, air having a dew point of −5° C. was flown into the tube for 3 minutes at the linear velocity of 3 m/min to dry.

Comparative Example 2

There was prepared a tube comprising 72.0 parts by weight of di-2-ethylhexyl phthalate (DOP) to 100 parts by weight of poly(vinyl chloride) resin and having the inner diameter of 6.4 mm, the outer diameter of 11.0 mm and the total length of 10 m. The resulting tube was subjected to a surface treatment using the surface treating agent 1 in a concentration of 0.3 wt %. Said tube was made into a loop of 30 cm radius as shown in FIG. 1, then 13 mL of the surface treating agent 1 in said concentration was placed therein. The tube was moved at the speed of 2.8 m/min and the surface treating agent 1 was flown therein until it reaches the outlet side. After removing the residual surface treating agent, air having a dew point of 0° C. was flown into the tube for 3 minutes at the linear velocity of 2 m/min to dry.

Comparative Example 3

There was prepared a tube comprising 72.0 parts by weight of di-2-ethylhexyl phthalate (DOP) to 100 parts by weight of poly(vinyl chloride) resin and having the inner diameter of 6.4 mm, the outer diameter of 11.0 mm and the total length of 10 m. The resulting tube was subjected to a surface treatment using the surface treating agent 1 in a concentration of 0.3 wt %. Said tube was made into a loop of 30 cm radius as shown in FIG. 1, then 13 mL of the surface treating agent 1 in said concentration was placed therein. The tube was moved at the speed of 2.8 m/min and the surface treating agent 1 was flown therein until it reaches the outlet side. After removing the residual surface treating agent, air having a dew point of −45° C. was flown into the tube for 3 minutes at the linear velocity of 63 m/min to dry.

TABLE 1

|  | Example 1 | Example 2 | Example 3 | Example 4 | Example 5 | Example 6 | Example 7 |
|---|---|---|---|---|---|---|---|
| Inner diameter (mm) | 12.7 | 6.4 | 12.7 | 6.4 | 12.7 | 12.7 | 12.7 |
| Outer diameter (mm) | 17.3 | 11.0 | 17.3 | 11.0 | 17.3 | 17.3 | 17.3 |
| Ra (μm) Inner surface | 0.012 | 0.034 | 0.012 | 0.034 | 0.012 | 0.012 | 0.025 |
| Outer surface | 0.010 | 0.042 | 0.010 | 0.042 | 0.010 | 0.010 | 0.011 |
| Coloration (hazen units) | 60 | 60 | 60 | 60 | 60 | 60 | 60 |
| Concentration of surface treating agent (wt %) | 0.3 | 0.3 | 0.2 | 0.2 | 0.3 | 0.2 | 0.2 |
| Feeding amount (mL/m) | 4.3 | 1.3 | 4.3 | 1.3 | 4.3 | 4.3 | 4.3 |
| Feeding speed (m/min) | 3.8 | 2.8 | 3.8 | 2.8 | 3.8 | 3.8 | 3.8 |
| Air linear velocity (m/min) | 16 | 63 | 16 | 63 | 3 | 16 | 16 |
| Air dew point (° C.) | −15 | −15 | −45 | −45 | −15 | −45 | −45 |
| ΔL | 0.98 | 0.83 | 0.82 | 0.65 | 0.098 | 0.070 | 0.069 |
| Oil defect | Not noted | Not noted | Not noted | Not noted | Noted | Not noted | Not noted |
| Endotoxin | Not found | Found | Not found | Not found | Found | Not found | Not found |

TABLE 2

|  | Comparative Example 1 | Comparative Example 2 | Comparative Example 3 |
|---|---|---|---|
| Inner diameter (mm) | 12.7 | 6.4 | 6.4 |
| Outer diameter (mm) | 17.3 | 11.0 | 11.0 |
| Ra (μm) Inner surface | 0.012 | 0.034 | 0.110 |
| Outer surface | 0.010 | 0.042 | 0.125 |
| Coloration (hazen units) | 60 | 60 | 50 |
| Concentration of surface treating agent (wt %) | 0.6 | 0.3 | 0.3 |
| Feeding amount (mL/m) | 4.3 | 1.3 | 1.3 |
| Feeding speed (mL/min) | 3.8 | 2.8 | 2.8 |
| Air linear velocity (m/min) | 3 | 2 | 63 |
| Air dew point (° C.) | −5 | 0 | −45 |
| ΔL | 9.32 | 1.52 | 1.05 |
| Oil defect | Noted | Noted | Not noted |
| Endotoxin | Found | Found | Not found |

INDUSTRIAL APPLICABILITY

In the medical tube according to the present invention, aggregation of an antithrombotic material is suppressed when said material is coated on the medical tube surface whereby appearance defect due to whitening can be reduced. In addition, since due consideration is paid on the condition for coating the material, occurrence of oil defect can be reduced.

Therefore, the medical tube according to the present invention certainly contributes to the development of the industry.

The invention claimed is:

1. A medical tube, comprising:
   a tube prepared by a melt extrusion molding of a composition comprising a thermoplastic resin and a plasticizer, and
   an antithrombotic material coated on an inner surface of the tube,
   wherein the difference (ΔL) between the brightness of the medical tube before coating and the brightness of the medical tube after coating measured in accordance with JIS Z 8722 is 1 or less,
   wherein the thermoplastic resin is poly(vinyl chloride),
   wherein the inner diameter of the tube is 2 to 20 mm, and
   wherein the thickness of the tube is 1 to 3 mm.

2. The medical tube according to claim 1, wherein no oil defect is found on the tube surface.

3. The medical tube according to claim 1, wherein the antithrombotic material is a heparin compound or a copolymer of hydrophobic (meth)acrylate with hydrophilic (meth)acrylate.

4. The medical tube according to claim 2, wherein the antithrombotic material is a heparin compound or a copolymer of hydrophobic (meth)acrylate with hydrophilic (meth)acrylate.

* * * * *